US005206176A

United States Patent [19]
Beér et al.

[11] Patent Number: 5,206,176
[45] Date of Patent: Apr. 27, 1993

[54] DETECTION AND CONTROL OF AROMATIC COMPOUNDS IN COMBUSTION EFFLUENT

[75] Inventors: János Beér, Winchester, Mass.; Arslan Kahn, Princess Anne, Md.; Adel F. Sarofim, Milton, Mass.; Jan H. Thijssen, Cambridge; Majed A. Toqan, Wellesley, both of Mass.

[73] Assignee: Massachusetts Institute of Technology, Cambridge, Mass.

[21] Appl. No.: 591,721

[22] Filed: Oct. 2, 1990

[51] Int. Cl.$^5$ ............................................ G01N 21/64
[52] U.S. Cl. .................................... 436/140; 436/124; 436/55; 436/172; 73/23.31; 110/344; 110/345; 110/185; 431/76; 356/318
[58] Field of Search ................. 436/52, 124, 139, 140, 436/55, 172; 73/23.31; 356/318; 431/76; 110/344, 345, 185

[56] References Cited

U.S. PATENT DOCUMENTS 4,038,032 7/1977 Brewer ........................... 23/230 A
4,293,521 10/1981 Isahaya .................................. 422/62

OTHER PUBLICATIONS

Di Lorenzo and Masi, "Formation and Evolution of Polycyclic Aromatic Hydrocarbons in Soot Forming Flames", p. 368 (1975).
Beer, "Stationary Combustion: The Environmental Leitmotiv, 22D Symposium (International) on Combustion/The Combustion Institute", 1988/pp. 1-16.
Beretta, "Laser Excited Fluorescence Measurements in Spray Oil Flames for the Detection of Polycyclic Aromatic Hydrocarbons and Soot", Combustion, Science and Technology, 1982, vol. 27, pp. 113-122.
Beretta, "Soot and Pah Distributions in Oil Spray Flames, Inferred by Elastic and Inelastic Laser Light Scattering", 19th Symposium (International) on Combustion/The Combustion Institute 1982, pp. 1359-1367.
Beretta, "Ultraviolet and Visible Fluorescence in Fuel Pyrolysis Regions of Gaseous Diffusion Flames", Combustion and Flame, 61:211-218 (1985).
Chaung, "Carbon Monoxide Burnout in Fluidized Coal Combustion", Oxidation Communications, 5 No. 3-4, 263-280 (1983).
Coe, "Laser Induced fluroescence of Polycyclic Aromatic Hydrocarbons in a Flame", Laser Probes for Combustion Chemistry, 1980, American Chemical Society, p. 158.
Crosley, "Laser Diagnostics and Modeling of Natural Gas Ignition Chemistry", 1986 International Gas Research Conference, p. 1177.
D'Alessio et al., "Laser Light Scattering and Fluorescence in Fuel Rich Flames: Techniques and Selected Results", Nato Conference Series (series) 6: Materials Science V7 (Proceedings of Nato) p. 355-378.
Toqan, "Pah and Soot Formation in Fuel-Rich Turbulent coal Liquid and Natural Gas Diffusion Flames", 20th Symposium (Int.) on Combustion/The Combustion Inst. 1984, pp. 1075-1081.
Di Lorenzo et al., "UV Absorption, Laser Excited Fluorescence and Direct Sampling in the Study of the Formation of Polycyclic Aromatic in Rich CH4/02 Flames", 18th Symp. (Int) on Combustion (1981).

(List continued on next page.)

Primary Examiner—James C. Housel
Assistant Examiner—David Redding
Attorney, Agent, or Firm—Fish & Richardson

[57] ABSTRACT

Detecting the presence of PAC's in the effluent of a combustions system by detecting the presence of a high molecular weight PAC's having five or more rings. A position along the effluent stream is selected at which high molecular weight PAC's may be present. The effluent is illuminated with radiation having a wavelength absorbed by the high molecular weight PAC's in the gas phase. The fluorescence from the illuminated effluent is detected, and analyzed by comparison to the known fluorescence of high molecular weight PAC's in the gas phase to determine the presence of the PAC's in the effluent. The effluent composition may be controlled in response to the detection.

31 Claims, 9 Drawing Sheets

OTHER PUBLICATIONS

Gomez, "Comparative Study of Soot Formation on the Center Line of Axisymmetric Laminar Diffusion Flames: Fuel and Temperature Effects", Combustion and Flame 69:225-241 (1987).

Miller et al., "Detection of Large Hydrocarbons in Diffusion Flames Using Laser Spectroscopy", Amer. Chem. Soc., St. Louis, MO Apr. 1984.

Miller, "The Observation of Laser-Induced Visible Fluorescence in Sooting Diffusion Flames", Combustion and Flame 47:205-214 (1982).

Muller, "Laser Induced Fluorescence: A Powerful Tool for the Study of Flame Chemistry", Laser Probes for Combustion Chemistry (1980), Chapter 5.

Salmon et al., "Measurement of Radical Species Concentrations and Polycyclic Aromatic Hydrocarbons in Flames by Fluorescence and Absorption Using a Tunable DI-Laser", Brookhaven Nat. Lab. (May 25, 1983).

Smyth, "Soot Inception in a Methane/Air Diffusion Flame is Characterized by Detailed Species Profiles", Combustion and Flame, 61:157-181 (1985).

Lawton, "The Effect of Gaseous Additives on LIF and Soot Volume Fraction in Premixed Flames", Chemical and Physical Proc. in Combustion (Proceedings From Fall Tech. Meeting) (1984), p. 100-1 100-3.

DETECTION AND CONTROL OF AROMATIC COMPOUNDS IN COMBUSTION EFFLUENT

FIELD OF THE INVENTION

This invention relates to the detection and control of aromatic compounds in combustion effluent

BACKGROUND OF THE INVENTION

Polycyclic aromatic compounds (PAC's), which may be emitted with the effluent of combustion systems represent a potential health hazard Some of these compounds have been shown to be toxic in laboratory tests. Dioxins, for instance, have caused severe damage to animal and plant life in laboratory experiments.

Laser induced fluorescence (LIF) is a technique which has been used in combustion research in carefully controlled laboratory-type environments for the detection of aromatic compounds in flames. In LIF, a laser photon is absorbed by a molecule and is thereby elevated to a higher electronic energy level. After some time, the excited molecule descends to a lower level. The difference in energy between the excited and non-excited states is emitted in the form of a photon.

SUMMARY OF THE INVENTION

It is an object of this invention to provide a method and apparatus for detection of aromatic compounds in combustion effluent of turbulent, diffusion flame combustion systems, such as practical, commercial combustion systems, by LIF and further to control effluent composition based on such detection.

Besides a fundamental lack of knowledge of the spectra of PAC's in the gas phase and the spectra obtained from LIF measurements in combustion systems, a general problem with LIF measurements is the ability to obtain adequate signal to noise ratio This may be a particular problem in the effluent from practical flames (e.g., turbulent diffusion flames) which have fuel rich mixture ratios within the combustion region causing optical noise from the sampling volume, including spontaneous radiation from particulates (e.g., ash and soot), and solid surfaces (e.g., furnace walls) These noise sources are inherent in the effluent of commercial-type incinerator systems which typically have soot and fly-ash loadings (up to 10 grams/m$^3$ of the effluent in turbulent diffusion flames) and dirty environments.

We have discovered that LIF of PAC's can be measured in the effluent of combustion systems, including the effluent from practical burner flames The presence and concentration of high molecular weight PAC's having five or more rings, can be related to the presence and concentration of other, harder to detect species such as dioxin. Detection of high molecular weight PAC's by LIF also enables real-time analysis and control of flame effluent by, for example, control of combustion conditions or injection of reactive species that inhibit PAC growth. In general, the LIF of high molecular weight PAC's having five or more rings can be detected from minute quantities of the PAC's, e.g., below 10 ppm (parts-per-million) or 1 ppm, down to 1 ppb (parts-per-billion) or less.

In preferred embodiments, the selection of the position for the measurement of PAC's by LIF is determined by two considerations. The positions may be chosen at a point along the effluent gas stream where the temperature has decreased to a level, e.g., 600° C. at which no further significant oxidation of residual PAC's in the effluent will take place. (Anything detected at that point can therefore be precipitated only by flue-gas treatment such as an active carbon filter or a catalyst but no further combustion reaction with air as an oxident is expected to occur) The other point of detection of PAC's by LIF may be effected further upstream in a temperature region of about 1200° C. in the oxidizing flame zone (but beyond the primary reaction zone); detection at this point is aimed at the early interception and destruction of PAC's so detected at a point further downstream by the injection of the reactant such as $O_2$, $H_2$, $H_2O_2$, etc.

"PAC's" as used herein refers to compounds having multiple aromatic rings and includes heteroatomic ring structures such as furans, and substituted ring structures, such as halogenated PAC's, for example, halogenated (e.g., chlorinated) dioxins, furans and polychlorinated biphenyls (PCB's). The rings of PAC's are directly fused or are bonded through non-aromatic ring structures. Examples of chlorinated dioxins include polychlorinated dibenzo(p)dioxin PCDD and 2,3,7,8, TCDD.

"High molecular weight PAC's", as used herein, refers to PAC's having five or more aromatic and/or nonaromatic rings, preferably, seven or more aromatic and/or nonaromatic rings. Examples of high molecular weight PAC's include coronene (seven rings), and others as discussed below.

An aspect of the invention is a method for detecting the presence of PAC's in the effluent of a combustion system. The method includes detecting the presence in the effluent of high molecular weight PAC's having five or more rings by selecting a position along the effluent stream at which the high molecular weight PAC's may be present and illuminating the effluent from the position with radiation having a wavelength absorbed by the high molecular weight PAC's in the gas phase. The fluorescence from the illuminated effluent is detected and analyzed by comparison to the known fluorescence of high molecular weight PAC's in the gas phase to determine the presence of the high 10 molecular weight PAC's in the effluent In preferred embodiments, the method includes the following A position is selected along the effluent stream where the detected fluorescence is predominantly from the high molecular weight PAC's when the high molecular weight PAC's are present. The high molecular weight PAC's are detected in a concentration range of about 10 ppm or less. The effluent stream has a temperature of less than about 1200° C. and lower than the temperature at which substantial sooting occurs. The effluent temperature is about 250° C. The effluent temperature is between about 250° C. to 1200° C. The intensity of the fluorescence is analyzed and the intensity correlated with the concentration of the PAC's. The fluorescence from the high molecular weight PAC's is correlated with the presence of other PAC's. The intensity of the fluorescence is correlated with the concentration of the other PAC's. The PAC's are selected from the group consisting of chlorinated dioxins and furans and PCB's.

In preferred embodiments, the method also may include effecting the composition of the effluent in response to the detecting and analyzing. The effecting may include injection of reactive species into the effluent. The position along the effluent stream of detection is selected such that injection of the reactive species can occur downstream of the selected position for real-time control of the effluent The effecting may also include controlling the conditions of combustion.

Preferred embodiments may also include the following. The high molecular weight PAC's have seven rings or more The high molecular weight PAC's are selected from the group consisting of cyclopenta [cd] pyrene, 1,3 diindopyrene, Benzo(b)fluoranthene, Benzo(k)fluoranthene, Benzo(a)pyrene, Benzo(ghi)perylene, 1,2,3, 1',2',3' diindopyrene, Anthanthrene, Coronene, benzo(a)coronene, Benzo(n)perylene, Naphto coronene, and Ovalene. The effluent is illuminated with radiation having a wavelength between about 400 to 515 nm. The wavelength is about 488 nm. The radiation is provided by a laser. The detected fluorescence is in the range from the illuminating wavelength to about 650 nm.

In another aspect, the invention features an apparatus for detecting the presence of PAC's in the effluent of a combustion system. The apparatus includes sampling means adapted to sample the effluent stream at a position where the effluent may include high molecular weight PAC's having five or more rings. An illuminating means is constructed to illuminate the effluent with radiation having a wavelength absorbed by the high molecular weight PAC's in the gas phase. Detector means is provided for detecting the fluorescence signal from the illuminated effluent and an analyzer means is provided for analyzing the signal by comparison to the known fluorescence signal of high molecular weight PAC's in the gas phase.

Preferred embodiments may also include the following. The illumination means is adapted for positioning along an effluent exhaust conduit and the illuminating means and detector are constructed and arranged such that the effluent is illuminated by a beam passing through a single aperture in the wall of the conduit and the fluorescence passing through the aperture is detected The beam is passed through the aperture at a first angle and the detector is positioned at a second angle with respect to the beam. The apparatus constructed and arranged to effect a sampling volume of about 0.1 to 5cm$^3$. The illuminating means is constructed to illuminate the effluent with radiation having a wavelength between about 400 to 515 nm. The illuminating means is a laser. The detector is constructed to detect fluorescence at a wavelength greater than the illuminating wavelength. The high molecular weight PAC's have seven or more rings.

In preferred embodiments, the apparatus may also include the following. A controller is provided for effecting the amount of the PAC's in the effluent in response to the detecting and analyzing. The controller is constructed to control the conditions of combustion. The controller is constructed to inject reactive species into the effluent. The analyzer is further constructed to analyze the intensity of the fluorescence and correlate the intensity with the concentration of the high molecular weight PAC's. The analyzer is adapted to correlate the presence of the high molecular weight PAC's with other PAC's. The analyzer is further constructed to correlate the intensity of the fluorescence with concentration of the other PAC's. The halogenated hydrocarbons are selected from the group consisting of chlorinated dioxins and furans and PCB's.

In another aspect, the invention features a method for detecting the presence of dioxins in the effluent of a diffusion flame combustion system. The effluent from a position along the effluent stream where the effluent has a temperature in the range below about 1200° C. is illuminated with laser radiation having a wavelength absorbed by high molecular weight PAC's having five or more rings in the gas phase. The laser induced fluorescence signal from the effluent is detected. The signal is analyzed by comparison to the known fluorescence of high molecular weight PAC's in the gas phase and the fluorescence from the high molecular weight PAC's is correlated with the presence of the dioxins.

In another aspect, the invention features a method for controlling the production of aromatic hydrocarbons in a commercial combustion system having a diffusion flame. The effluent from a position along the effluent stream having a temperature below about 1200° C. is illuminated with radiation having a wavelength absorbed by high molecular weight PAC's in the gas phase having five or more rings. The laser induced fluorescence from the effluent is detected and the composition of the effluent is effected in response to the detecting. In preferred embodiments, the conditions of combustion are controlled or reactive species into the effluent.

In another aspect, the invention features a method for detecting the presence of high molecular weight PAC's having five or more rings in a gas-phase concentration range of about 10 ppm or less by illuminating the high molecular weight PAC's with radiation having a wavelength absorbed by the high molecular weight PAC's in the gas phase, detecting the fluorescence from the illuminated PAC's and analyzing the fluorescence to determine the presence of the high molecular weight PAC's in the effluent.

Preferred embodiments include the following. The concentration range may be below 1 ppm or about 1 ppb or less. The high molecular weight PAC's have more than seven rings.

Other embodiments and advantages follow.

DESCRIPTION OF THE PREFERRED EMBODIMENTS

We first briefly describe the drawings.

DRAWINGS

STRUCTURE

The LIF of high molecular weight PAC's can be measured in the effluent of combustion systems downstream of the flame or combustion region (i.e., the primary reaction zone where predominantly oxygen reacts with fuel). The sensitivity of the measurement enables detection of minute quantities of the PAC's, e.g. less than 10 ppm or 1 ppm, down to the parts per billion (ppb) range or lower, for real-time monitoring of combustion effluent and/or control of combustion conditions in optically noisy commercial combustion systems. Detection of PAC's in the flame effluent, beyond the flame or combustion region where varied and difficult to predict pyrolysis reactions taken place, provides a reliable measure of the environmental contribution of these species, since the likelihood of reaction downstream from the sampling position is reduced. Further high molecular weight PAC's, as contemplated herein, are "refractory", i.e., they are comparatively resistant to reaction or degradation under conditions in the effluent and thus, for this reason as well detection of such species represents a confident measure of environmental contribution. The presence and concentration of high molecular weight PAC's, as detected by LIF can be related to the presence and concentration of other combustion byproducts, which are present in even lower quantities and/or are generally difficult to detect by LIF, for example, dioxins.

Figure 1:
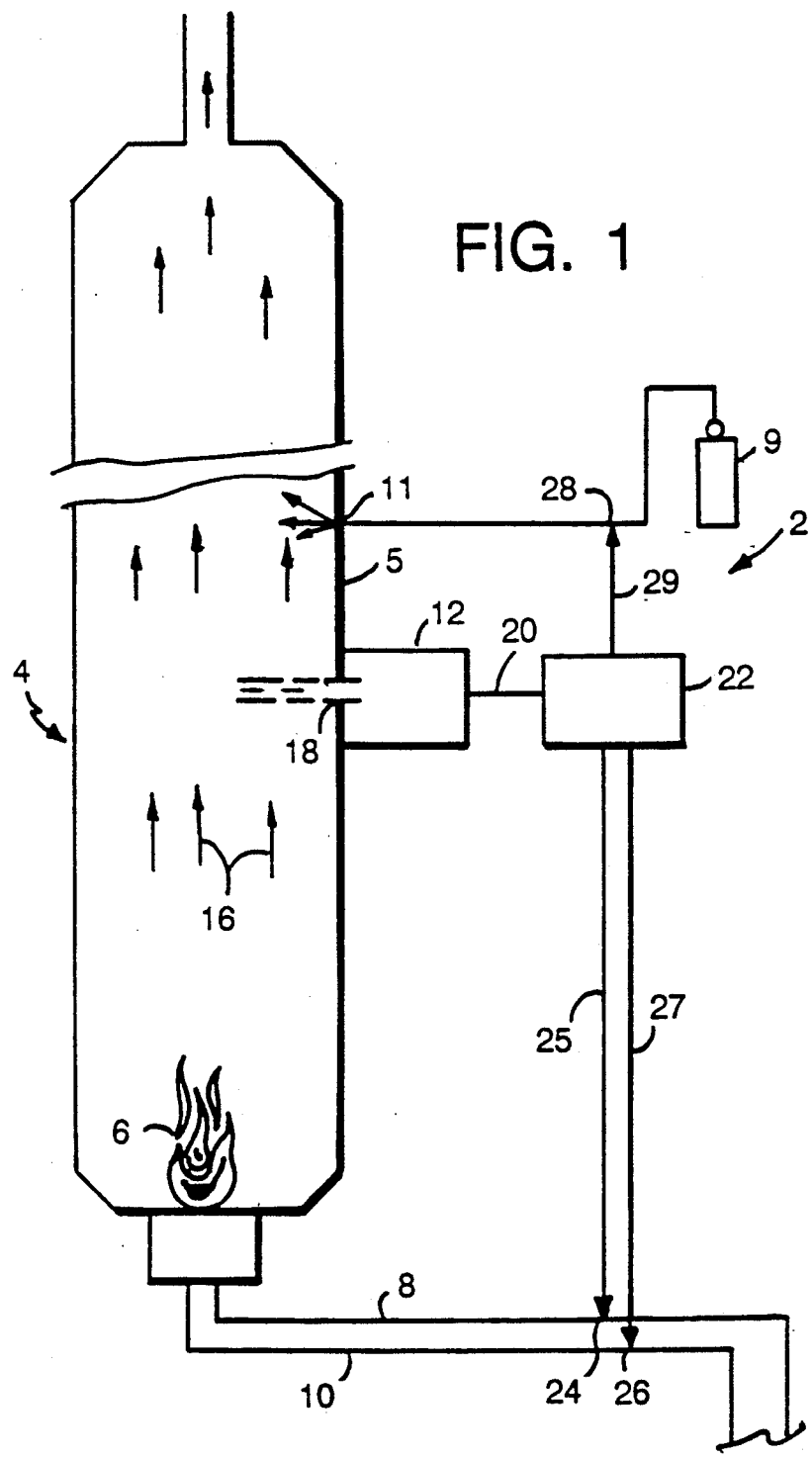
FIG. 1 is a schematic of an LIF detection and control apparatus according to the invention, installed on a commercial combustion system.

Referring to FIG. 1, an LIF detection and control apparatus 2 according to the invention, is shown in place on a commercial combustion system 4. The combustion system may be, for example, a coal, gas, or oil burning utility boiler or a waste incinerator. The system includes a combustion region 6 fed by fuel lines 8,10 and a flue duct 5, through which the effluent 16 from the combustion region travels to be eventually exhausted to the atmosphere. The LIF apparatus 2 includes an optical assembly 12 positioned alongside the flue gas duct 5 at an optimal point for the detection of the LIF from the desired high molecular weight PAC species.

Optical unit 12 directs laser beam 14 into the path of the combustion effluent 16 and further includes detection means (FIG. 2) for detecting the fluorescence emitted by the effluent. The laser beam and fluorescence emission are passed from and received by the optical system 12 through a single optical port 18 in sidewall of the flue-gas duct 5 (or the combustion chamber, as desired) The detected fluorescence signal is delivered via line 20 to analyzer and control unit 22 which determines, from the fluorescence signal, the presence and concentration of PAC's and, in response thereto, controls, via lines 25, 27, valves 24,26 on the combustion system fuel lines 8,10 to vary the fuel characteristics and reduce the production of undesirable compounds, e.g., PAC's and chlorinated aromatics such as dioxins. For example, the fuel equivalence ratio may be varied to reduce the PAC emission as discussed in Beer, J. M., W. F., Farmayan, J. D. Teare and M. A. Toqan: "Laboratory Scale Study of the Combustion of Coal-Derived Liquid Fuels". *EPRI Report.* AP4038, 1985. 182 pages.

The control system 22 can also actuate valve 28 via line 29 to control the injection of reactive species such as oxygen, hydrogen peroxide, air, hydrogen, ammonia or methane from a tank 9, into the effluent stream at a port 11 where reaction with the pollutants of concern (e.g., PAC's) effects the reduction of undesirable combustion-produced species. As illustrated, the injection port 11 may be located downstream of the detection means 2 to control the composition of the effluent in a real time manner, i.e., the effluent analyzed is effected before release to the atmosphere.

Figure 2:
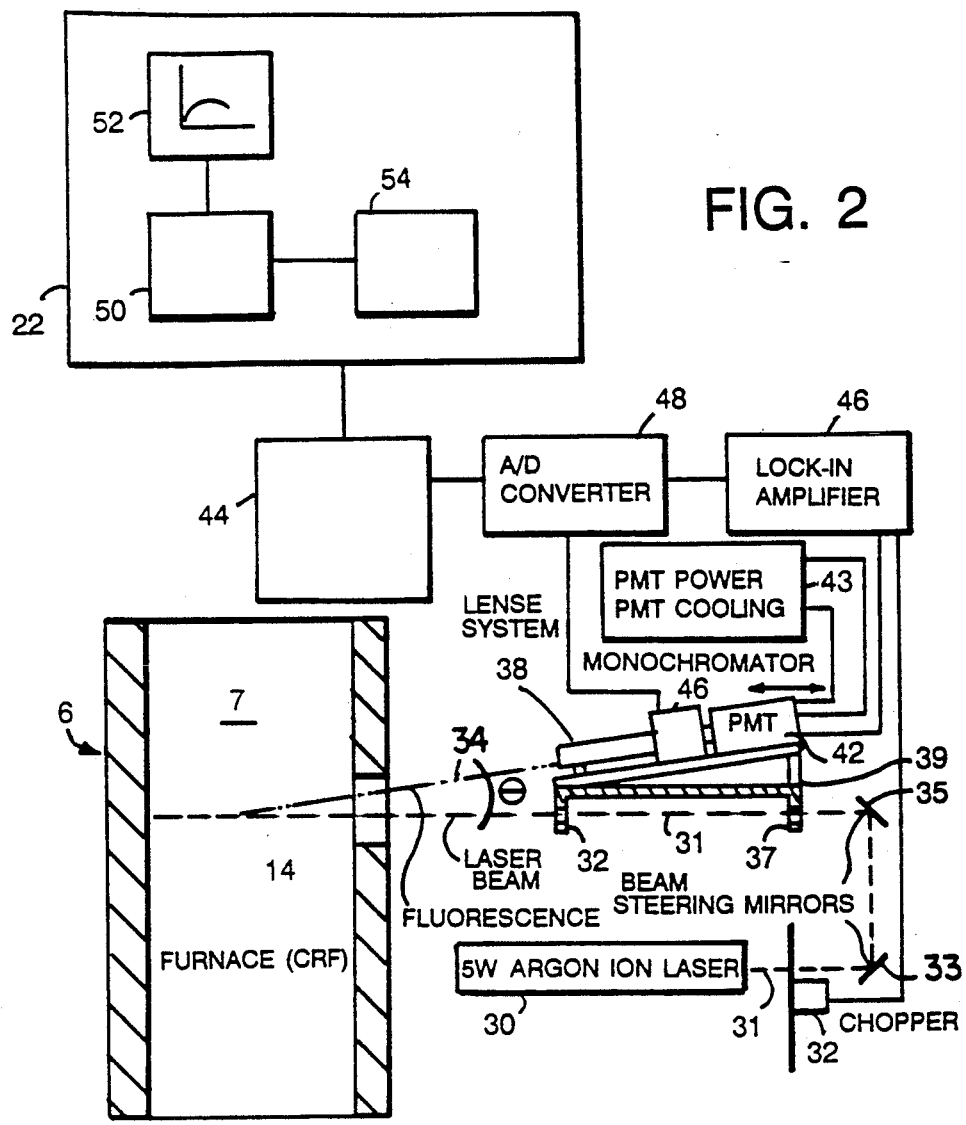
FIG. 2 is an enlarged view of the LIF apparatus as in FIG. 1, illustrating optical and electrical components.

Referring now to FIG. 2, a 5 watt continuous wavelength argon ion laser 30 is used as a light source at a beam wavelength of 488 nm. The output beam 31, about 3 mm in diameter, is modulated by a light chopper 32 at a frequency of 1100 Hz and directed into the interior 7 of the exhaust duct 5. The beam is directed by steering mirrors 33, 35, through optical ports 37 in optical bench 39 and finally through the port 18 in the burner side wall. Preferably, LIF emission from high molecular weight PAC's is detected in the ultraviolet and/or visible range, more preferably from about 450 nm to 650 nm. Wavelengths for fluorescence excitation of high molecular weight PAC's in combustion effluent, may also be in the visible, for example, between 450 nm to 650 nm, preferably from 450 to 515 nm, for which a tunable laser source might be employed A pulsed laser might also be used The detected fluorescence may be, in general, mainly in the wavelength range higher than the excitation wavelength An illumination source other than a laser, if of sufficient intensity may also be employed.

The optical components have been arranged to provide a compact, apparatus that requires only a single aperture to the exhaust duct The laser beam 31 is directed through the port 18 at a first angle, for example, about normal to the effluent flow, while the LIF from the effluent is detected through the port 18 at an angle off-set from the beam input angle $\theta$, e.g., about 10 degrees (The half angle of the cone detected is preferably 3.1°). The port 18 is transparent to the radiation at the laser and emission wavelengths and may be, for example, an open aperture in the furnace sidewall or a window formed of a heat resistant, transparent material such as quartz. The port 18 is larger than the beam width to enable the detector to optically access the beam sampling volume, in a preferred embodiment the port 18 is about 30 cm in diameter. Good signal to noise ratio of the LIF signal is achieved by effecting a sampling volume (a cylindrical region of about $60 \times 3$ mm in a typical system) of about 0.5 cm$^3$. The detector may be made moveable with respect to the beam axis (as indicated by the arrow) for sampling fluorescence at various axial positions of the effluent stream. (It will be understood multiple optical ports may also be used).

The signal 34 from the sampled volume in the furnace, which includes fluorescence and scattering is collected by a lens system 38 including a lens (not shown) which focusses the fluorescence emission on an aperture or slit (not shown). In front of the detector a filter (not shown) for rejection of the incident beam wavelength is placed to eliminate scattered light. A monochromator 40 (0.25 m focal length) is used to scan the effluent fluorescence. In case of operation without a monochromator additional filters could be used for wavelengths selected. When using a pulsed laser, discrimination can be made between fluorescent and other laser induced radiation by recognizing the characteristic delay of fluorescent emission following the incidence of laser radiation. Further discrimination can be made based on the depolarizing character of laser induced fluorescence; if the laser beam is polarized a polarization analyzer at the detector could distinguish between fluorescent (non polarized) and other (polarized) radiation.

Filtered light reaches the photomultiplier tube (PMT) 42 (having separate power and cooling means 43, e.g., liquid nitrogen or thermoelectric) after wavelength selection by the monochromator 40. The signal from the PMT is amplified by a lock-in amplifier 46 which is locked in to the reference signal from the light chopper 32 to eliminate background noise from the signal. The amplified and "clean" signal is digitized with A/D converter 48 and reported to data acquisition system 44.

The signal in analogue or digital form is reported to controller 22 which typically includes an analysis means 50 for analyzing the LIF signal collected. Analyzer 46 performs a comparator function to determine the presence of high molecular weight PAC's by comparison of the detected LIF signal to the LIF signal of known high molecular weight PAC's, in the gas phase, preferably, at effluent temperatures. In addition, the LIF signal may be analyzed quantitatively to determine the concentration of high molecular weight PAC's in the effluent by analysis of the intensity of the signal and comparison to an intensity versus concentration curve, determined from prior experiment. A display such as a strip chart recorder or CRT may provide a histographic readout of the PAC concentration. The system 22 also includes controllers 54 that provide output to control the production of PAC's by controlling the combustion parameters or injection of reactants as discussed above, by signals sent over control lines 25, 27, 29. It will also be understood that the control system 22 and data acquisition means 44 may be, for example, a stand-alone computer, such as a personal computer. A single wavelength or narrow wavelength region might also be detected and correlated with the presence of high molecular weight PAC's.

THEORY AND OPERATION

Figure 3:
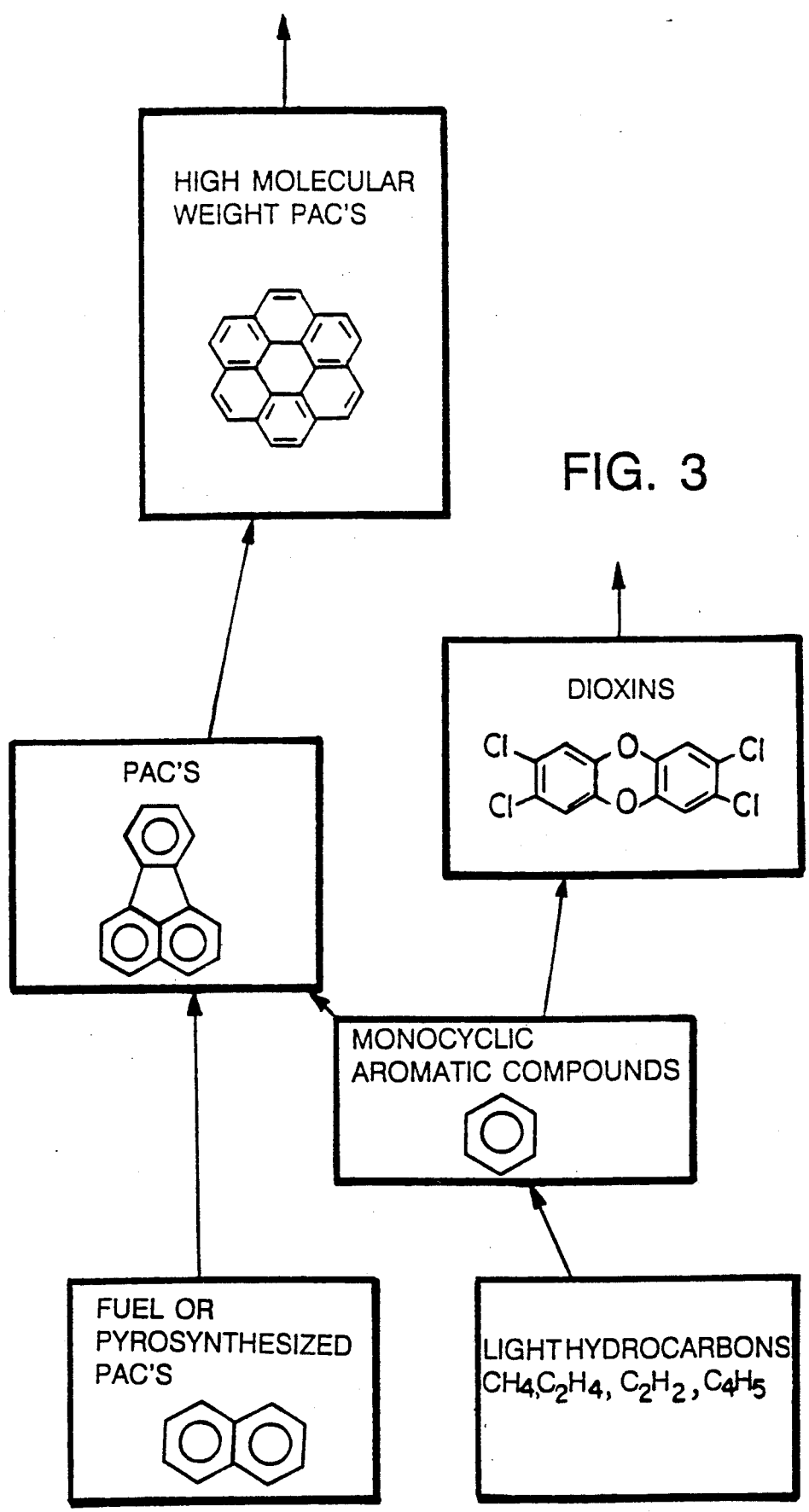
FIG. 3 is a flow diagram that illustrates a pyrolytic formation scheme for PAC's.

Referring now to FIG. 3, a formation scheme for PAC's in the effluent of a combustion system, beyond the flame or combustion region, as a function of the effluent temperature (and in general, the distance from the flame or combustion region) is illustrated. As a by-product of the combustion process, light hydrocarbons and their radicals are formed which recombine to form generally monocyclic, aromatic compounds. These species can further combine with other light hydrocarbons and, for example, fuel or pyrosynthesized PAC's to form other low molecular weight PAC species such as those having 2 to 4 rings which still further combine to produce high molecular weight PAC's (having 5 or more rings) to which substantial biological activity has been attributed. The stability of synthesized compounds increases at lower temperatures such as those found beyond the combustion region since the rate of oxidation of further reaction is reduced. At low temperatures, e.g., in the range of 250°-350° C., monocyclic aromatics react with other elements within the effluent to form highly toxic compounds such as dioxins and/or furans. The formation of dioxins is thought to primarily occur by surface catalyzed reactions of PAC precursors. It should be understood that under conditions in commercial combustion in which PAC's are often present in the fuel, the pyrosynthesis of high molecular weight species can occur at higher temperatures in the effluent and higher concentrations than in "cleaner" combustors (e.g., using pure methane) in which species such as benzene must be formed first so that high molecular weight species can by synthesized.

The presence of high molecular weight PAC's in combustion effluent can be detected by LIF. The optimal sampling position along the effluent stream may be selected based on several considerations. The effluent may be sampled beyond the flame or combustion region, i.e., beyond the pyrosynthesis region of the flame, at a point along the effluent stream where the effluent temperature is in a range at which high molecular weight PAC's are present and stable in the gas phase, i.e., less likely to undergo reactions such as cracking or reactive oxidation which results in the transformation downstream of the measurement. The effluent also may be sampled at a point where the effluent temperature is above the temperature at which the PAC's condense from the gas phase and below the temperature at which excessive sooting occurs, both of which effects reduce the sensitivity of LIF by removing PAC from the gas phase and extinguishing the fluorescence signal. However, even under high sooting conditions often found in commercial burners, the LIF from high molecular weight PAC's can still be detected.

In general, the LIF measurement apparatus may be positioned to sample the effluent downstream of the flame or combustion region, preferably at a point where the effluent temperature is between about 200°-1200° C., preferably at about 250°-500° C., more preferably in some embodiments at around 250° C. The LIF measurement apparatus may sample the effluent at regions where the combustion effluent is at lower temperatures, e.g., around 130° C., with low concentrations of PAC that are present in the gas phase due to the vapor pressure equilibrium. In a typical combustion system, of about 0.25 mw, the effluent is preferably sampled by LIF about 1 meter or more downstream from the primary reaction zone.

Detection of LIF at lower temperatures. e.g., in the range discussed above, may be particularly advantageous for monitoring the environmental contribution of high molecular weight PAC's since, at low temperatures, these refractory compounds are even less likely to react or degrade to other species. The measurement, therefore, represents the actual environmental contribution of high molecular weight PAC's from the effluent.

Detection of the LIF signal at higher temperatures, e.g., in the range discussed above, may be particularly advantageous in systems that control combustion conditions by injection of reactive species. In this case, the detection system, which enables an instantaneous measurement of high molecular weight PAC presence, could be positioned upstream of the injection apparatus to enable real-time control of combustion effluent. The instantaneous detection and control of effluent in this manner is particularly useful in burner systems where temporary or nonuniform combustion conditions, such as in the incineration of varieties of wastes, which results at various times in "puffs" of effluent containing toxins such as PAC's.

It will be understood that multiple LIF detection stations might be useful. For example, LIF analysis upstream and downstream of a reactive species injection port enables real-time control of effluent in response to the upstream analysis while confirmation of the efficiency of the effluent control by the injection system is provided by the downstream analysis A single downstream analysis system may also be used to determine the efficiency of the reactive injection and the LIF analysis used to feedback to modify the injection.

The effluent may be sampled from the stack and directed off-line to a sampling system such as a heated cell. It might also be advantageous to sample the effluent after a filter means such as a charcoal filter, intended to absorb PAC's. The high sensitivity of the LIF measurement for high molecular weight species is thus indicative of the efficacy of the filter and the environmental contribution.

It is desirable to sample the LIF from a position along the effluent stream where the high molecular weight PAC's are present in sufficient concentration (less than 1 ppb may be sufficient) and further the sampling should occur from a position at which the detected fluorescence can be attributed primarily to the high molecular weight PAC's of interest The position along the effluent stream for sampling in particular combustion systems may be determined by collecting samples of the effluent and determining the effluent composition. For example, the relative concentrations of high molecular weight and low molecular weight PAC's may be determined by conventional probe sampling and chemical analysis to select a position along the effluent stream such that substantial contribution of fluorescence from lower molecular weight PAC's such as acenaphthalene in the detected LIF signal is avoided or insignificant. In general, the gas phase, effluent temperature fluorescence signal from high molecular weight PAC's such as coronene (seven rings) is as much as orders of magnitude stronger than lower molecular weight PAC's such as naphthalene (2-rings), acenapthalene (3-rings), anthracene (3 rings), phenanthrene (3-rings), fluoranthene (3-rings) and pyrene (4-rings) depending on factors such as excitation wavelength. Proper selection of excitation wavelength also enables selective detection of high molecular weight PAC's. For example, naphthalene, acenaphthylene, phenanthrene and pyrene do not substantially fluoresce when excited at 488 nm, and fluoranthene fluorescence relatively weakly. High molecular weight PAC's such as coronene are strongly fluorescent at this excitation wavelength. In general, less flourescence is generated from low molecular weight species by higher wavelength excitation.

Because of the strong fluorescence of high molecular weight PAC's, (detectable at 1 ppb or less) these compounds may contribute substantial fluorescence even when lower molecular weight species which are also fluorescent, are present in higher concentrations. In some cases, at higher temperatures, low molecular weight PAC's such as acenaphthalene, which might contribute fluorescence to the detected signal, are generally in low concentration and are not substantial contributors to the detected LIF signal while the signal from high molecular weight PAC's which are present in even lower concentrations, might be detectable. In some systems, the concentration of low molecular weight PAC's peaks at some distance from the combustion region. It may be desirable to detect LIF at a position upstream or downstream from this peak when the concentration of low molecular PAC's begins to decrease The concentration of high molecular weight PAC's may peak at a position downstream from the low molecular weight peak in which case the high molecular weight peak could be an advantageous position for sampling. It may also be advantageous to sample the effluent at a point upstream from the low molecular weight concentration peak. In this case, while the high molecular weight species may be in low concentration, the intense fluorescence signal enables reliable detection since the low molecular weight PAC's which may be in higher concentration than the high molecular weight species, do not contribute significantly to the detected signal.

Further, the presence and concentration of high molecular weight PAC's can be related to the presence and concentration of other PAC's including low molecular weight PAC's (such as those from which the high molecular weight PAC's were synthesized, see FIG. 3) and toxins such as chlorinated hydrocarbons which are generally much harder to detect by LIF because of their low concentrations (typically 0.1 ppb (01.ng/m$^3$) or less) and poor fluorescing characteristics. High molecular weight PAC's can thus be detected as surrogates for these other PAC's in combustion processes.

The correlation between the LIF signal strength and the quantity of the high molecular weight PAC's may be determined by off-line LIF experiments in a heated cell using heat samples of PAC's. The LIF signal strength can also be correlated with a sum of PAC's present in the effluent. Correlation functions can be confirmed by simultaneous LIF and conventional probe sampling and analysis. The correlation of the LIF signal from high molecular weight PAC's with the presence and concentration of other PAC's such as dioxins may also be confirmed by conventional direct probe sampling and chemical analysis.

EXPERIMENTS

Example 1

The effect of temperature on the LIF signal of various neat high molecular weight PAC's and the detection limits by LIF were studied in a cell experiment. In the cell experiment, the LIF signal was determined for known high molecular weight PAC's injected into a heated cell at known concentration The LIF from a PAC species having less than 5 rings, (anthracene, 3 rings) was also measured to compare the LIF signal strength to high molecular weight PAC's.

Figure 4:
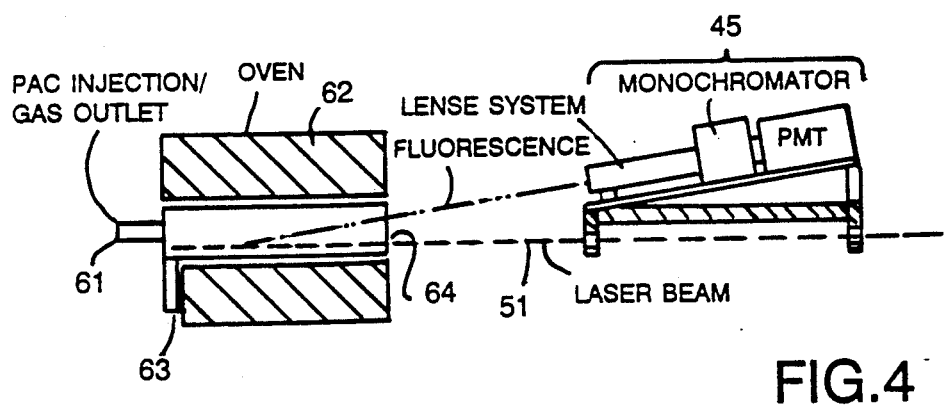
FIG. 4 is a schematic of a fluorescence cell used to detect the fluorescence of samples of known PAC's.

Referring to FIG. 4, the cell 60 is shown placed in an oven 62. The cell 60 has a window 64, an inlet 61 for injection of PAC samples which may be in a solvent such as dichloromethane and inlet 63 for purging with inert gas such as nitrogen. An optical system, substantially as described with respect to FIG. 2, provides a beam 31 and a detector system 45 detects the LIF signal from the window 64. Spectra were recorded at different temperatures and for different concentrations to determine temperature and concentration dependence and for determination of detection limits.

Figure 5:
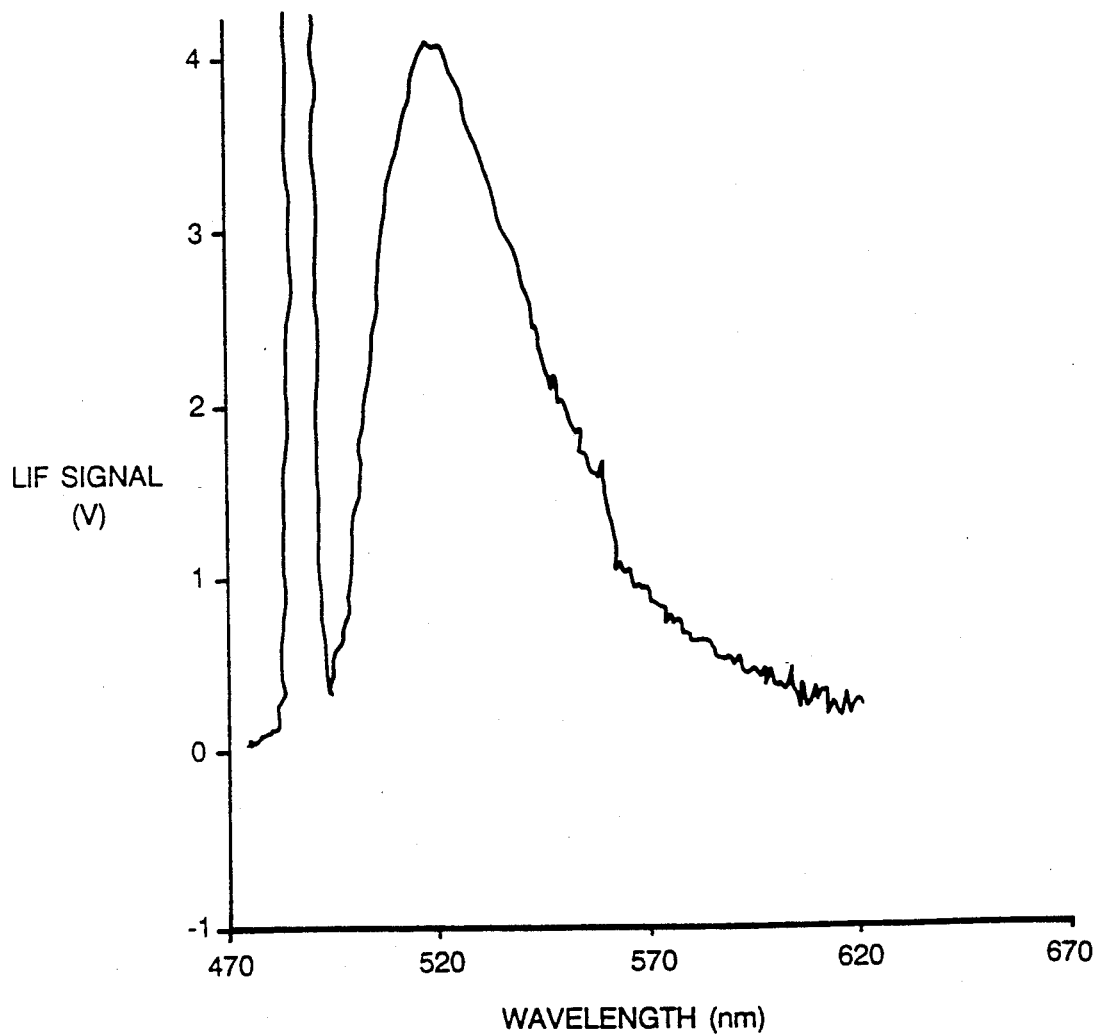
FIGS. 5-5b are an LIF spectra of a pure samples of PAC's.

Referring now to FIG. 5, an LIF signal from a sample of coronene, a high molecular weight PAC having seven rings, is shown at 800° C. at 10 PPm. Using an excitation wavelength of 488 nm, a scan was made from 480 nm to 630 nm in approximately 20 minutes. The data was processed by categorizing in bins of 1 nm spectral bandwith and averaged per bin. From those averages the spectrum shown was constructed between 495 and 630 nm to obtain the total fluorescence. The laser power output was kept at 1.3 W throughout the experiment and the signal was not normalized. In the amplification, a time constant of 0.3 sec was used to filter out high frequency fluctuations in the signal.

For coronene, quantitatively, the signal strength increased from 300° C. to 800° C. (thought to be due to increases in the vapor phase concentration) and decreased slightly from 800° to 1200° C. (thought to be due to pyrolysis) and the fluorescence spectrum did not vary significantly qualitatively over a temperature range of about 300° to 1200° C. The detection limit at 170° C. was determined to be at least about 1 ppb on a volume basis.

Figure 5A:
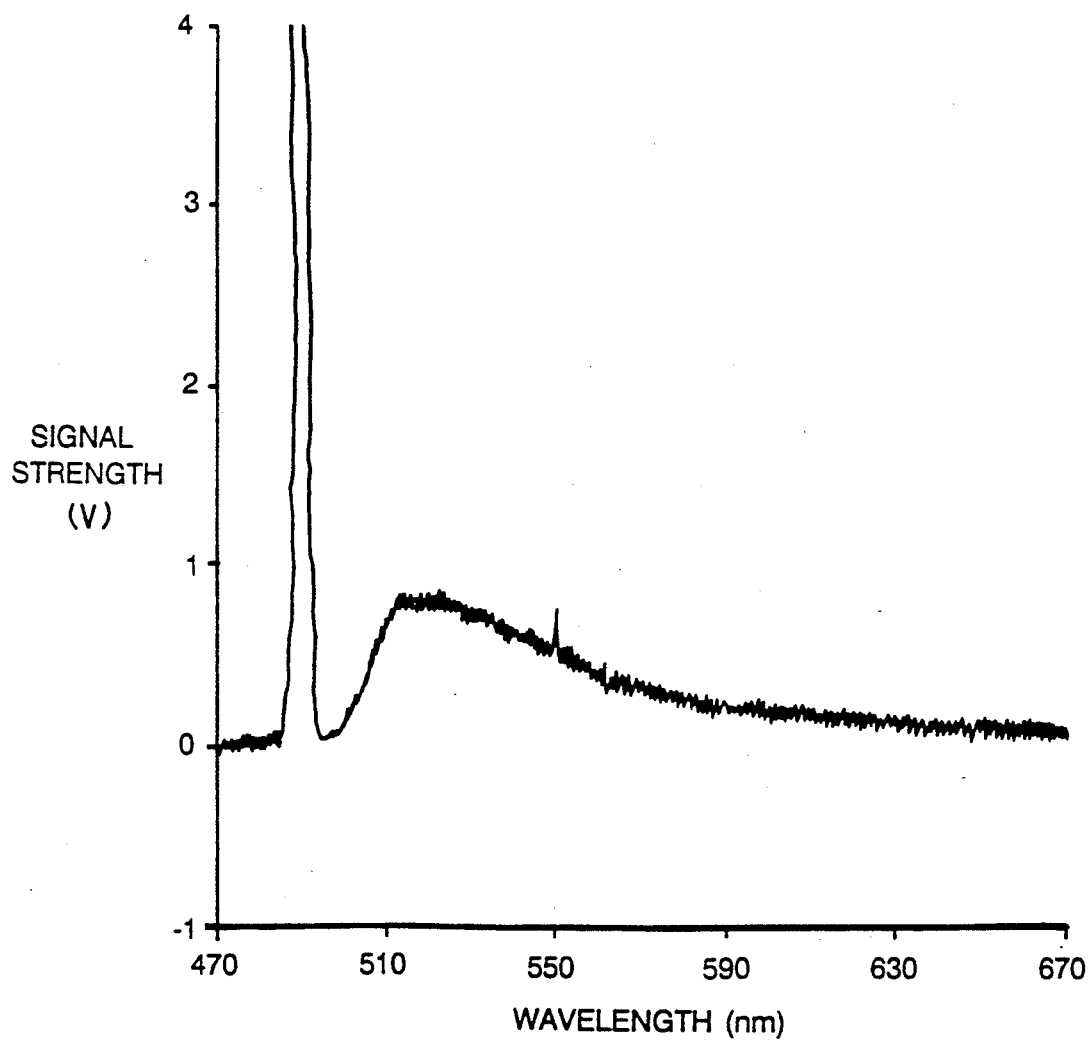

FIG. 5a shows the LIF spectrum for Benzo (GHI) perylene, a high molecular weight PAC having six rings. This spectra was taken using the optical parameters described above at a cell temperature of 170° C., with a sample concentration of 10 ppm.

Figure 5B:
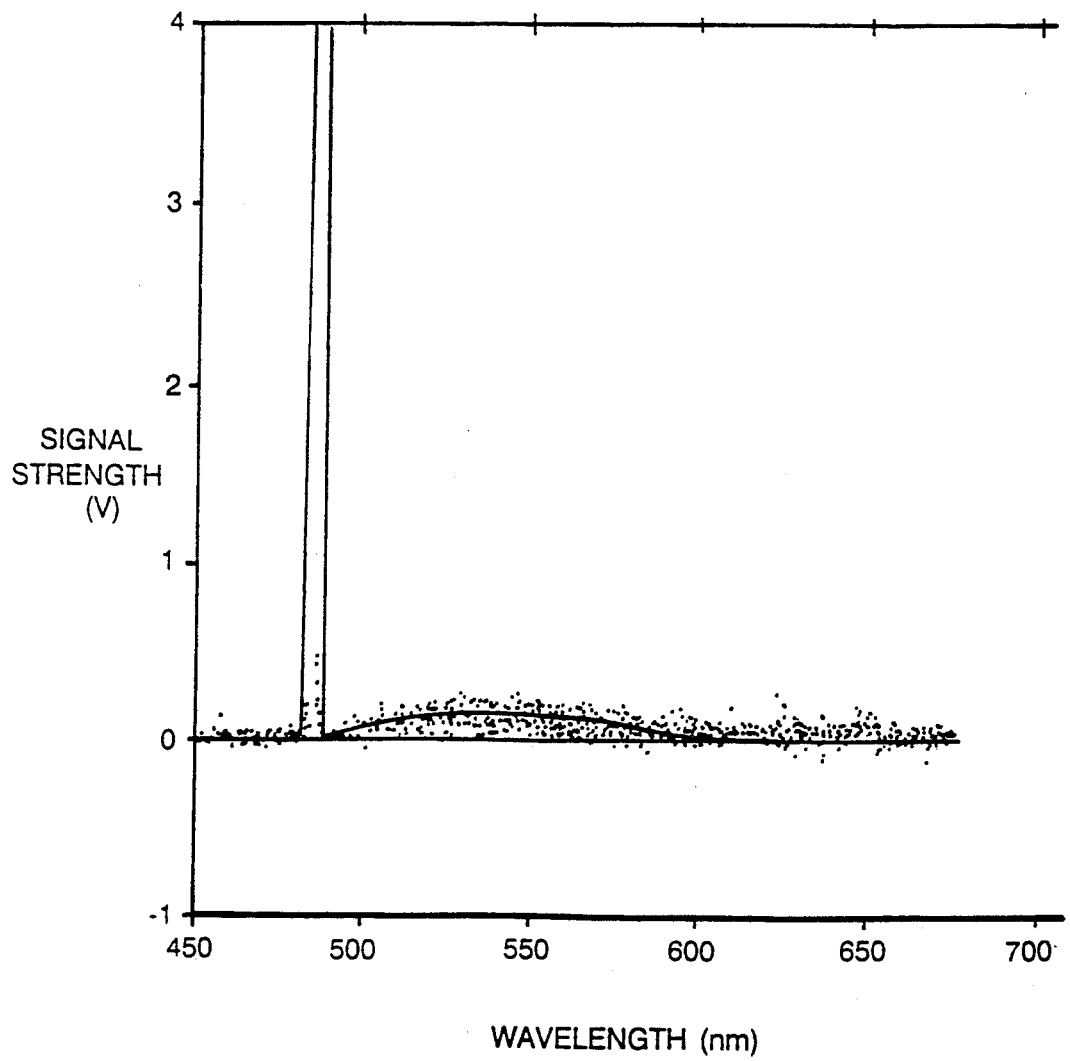

FIG. 5b shows the spectrum of anthracene, a PAC having 3 rings. This spectrum was taken using the optical parameters described above, at a cell temperature of 170° C., with a sample concentration of 100 ppm, a factor of ten higher than the spectra of the high molecular weight PAC's in FIGS. 5 and 5a.

As evident from the comparison of the spectrum of the PAC (three rings) in FIG. 5b, with the spectra of the high molecular weight PAC's in FIGS. 5 and 5a (seven and six rings, respectively) the fluorescent emission from the higher molecular weight PAC's is much higher despite the 10 fold greater concentration of the three ring PAC. (The fluorescence intensity scale is the same for FIGS. 5-5b). Sensitivity data from even a relatively strongly fluorescing low molecular weight PAC, fluorenthene (four rings) showed a detection limit of about a factor of four less than coronene.

Example 2

Fluorescence from the effluent generated in turbulent diffusion flames was measured using a combustion system installed at the MIT Combustion Research Facility, that is fully described in Beer et al., *EPRI Report*, supra. In brief, the combustion system is a pilot scale 3 megawatt thermal combustion burner adaptable for combustion of natural gas, petroleum distillates, coal, oil, solvent refined coal and pure compounds. In the present experiment, a toluene doped natural gas flame was employed.

Figure 6:
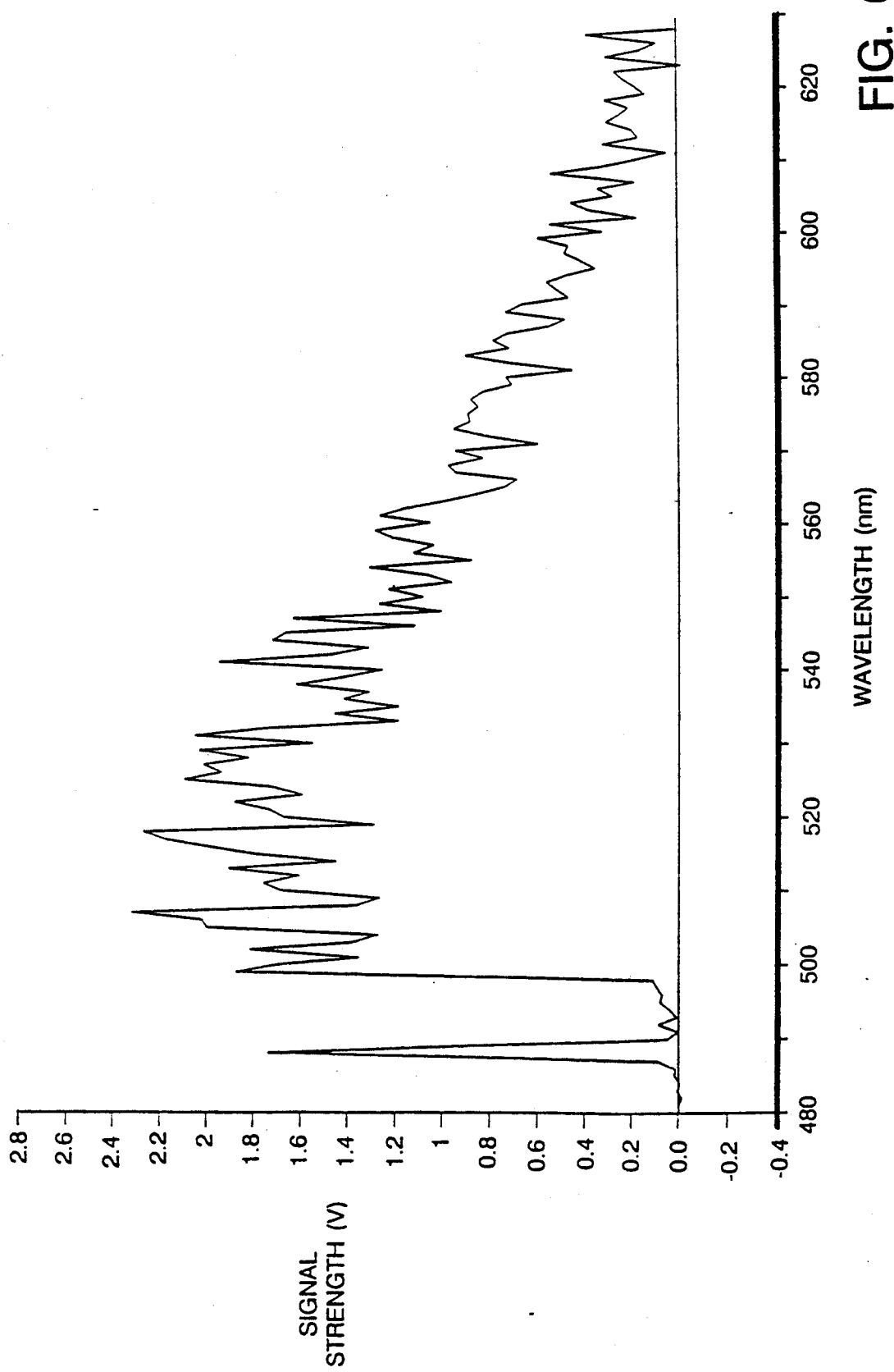
FIG. 6 is an LIF spectrum from a natural gas flame.

Referring now to FIG. 6, an LIF spectrum obtained from the large scale system is shown. The laser beam was introduced into the effluent duct about 3 meters downstream from the burner at which point the effluent temperature was about 1200° C. (about 2 m from the primary reaction zone). The peak at 488 nm is due to scattering which is a measure for the particulates concentration as discussed for example in F. Beretta, A. Cavaliere and A. D'Alessio: "Soot and PAH Distributions in Oil Spray Flames Inferred by Elastic and Inelastic Laser Light Scattering", Nineteenth Symposium (International) on Combustion, pp. 1354-1367, The Combustion Institute, 1982.

The fluorescence from pure high molecular weight compounds, e.g., coronene and Benzo (GHI) perylene obtained as discussed in Example 1 and the spectrum from the flame effluent give good correspondence. Coronene was also found in direct probe sampling and conventional chemical analysis experiments in which samples were collected at the same position along the effluent stream as the LIF was detected.

Example 3

Experiments were conducted in which the LIF signal was measured in a turbulent diffusion flame combustion system (as an Example 2) at various positions along the effluent stream and samples were collected by direct probe and chemically analyzed from the same positions along the stream to confirm the presence of and correlate the concentration of high molecular weight PAC's as a function of the LIF signal. Natural gas was introduced into the combustion chamber as the primary fuel and both toluene and methyl chloride were injected at a location close to the end of the natural gas flame in a region in which the temperature is about 1200° C. The fuel equivalence ratio in this primary stage was slightly fuel rich. Secondary air was added 3.4 m downstream of the burner and occasionally pure oxygen was injected at a distance of 5.3 m away from the burner to clean the flue gas stream from products of incomplete combustion before effluent was exhausted to the environment.

The LIF system used was substantially as discussed in regard to FIG. 2, including a 5 w laser fixed at 488 nm, a monochrometer able to scan wavelengths between 300 nm and 800 nm, a photo-multiplier, a lock-in amplifier, a system for data processing and a series of lenses for focusing the beam and the signal. The system was positioned at points corresponding to the points of conventional sampling.

Conventional sampling was carried out by collecting volatile organics and soot with a sampling system which includes a sampling probe, an ice trap to remove water and a three stage dichloromethane (DCM) trap to absorb organic compounds. The collected water was extracted with methylene chloride and then both extracts were combined and concentrated from about 900 ml to roughly 6 ml in a kuderna-Danish evaporative concentrator.

The collected concentrate was then analyzed using a Gas Chromatograph in series with either a Mass Spectrometer (GCMS), a Fourier transform infrared detector (GC-FTIR), or a flame ionization detector (GC-FID), and by a means of High Pressure Liquid Chromatography (HPLC), the latter mainly for identification of high molecular weight species. Details of the conventional sampling means are discussed in the MIT Combustion Facility NIEHS Annual Report, 1988.

Figure 7:
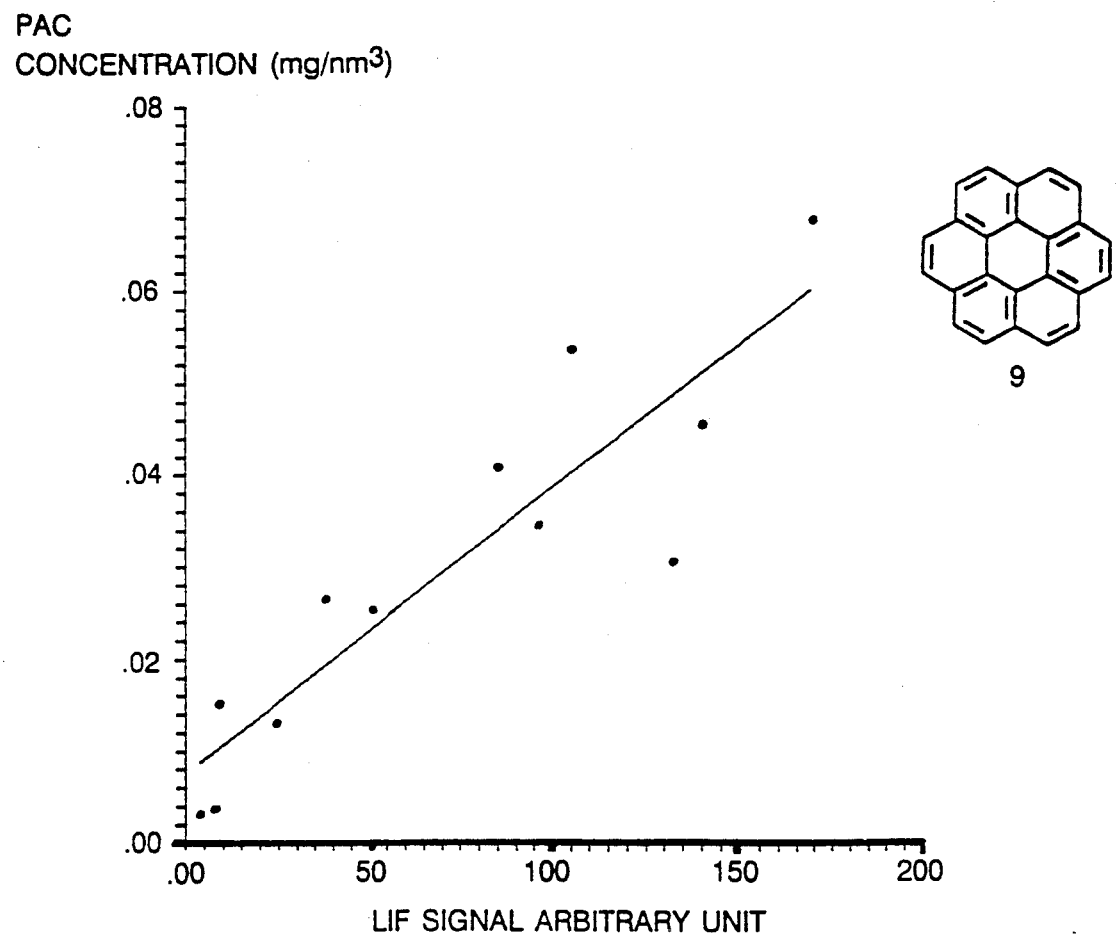
FIGS. 7-7a are graphs of the PAC concentration versus LIF signal from a combustion apparatus for coronene and a sum of PAC's, respectively.
Figure 7A:
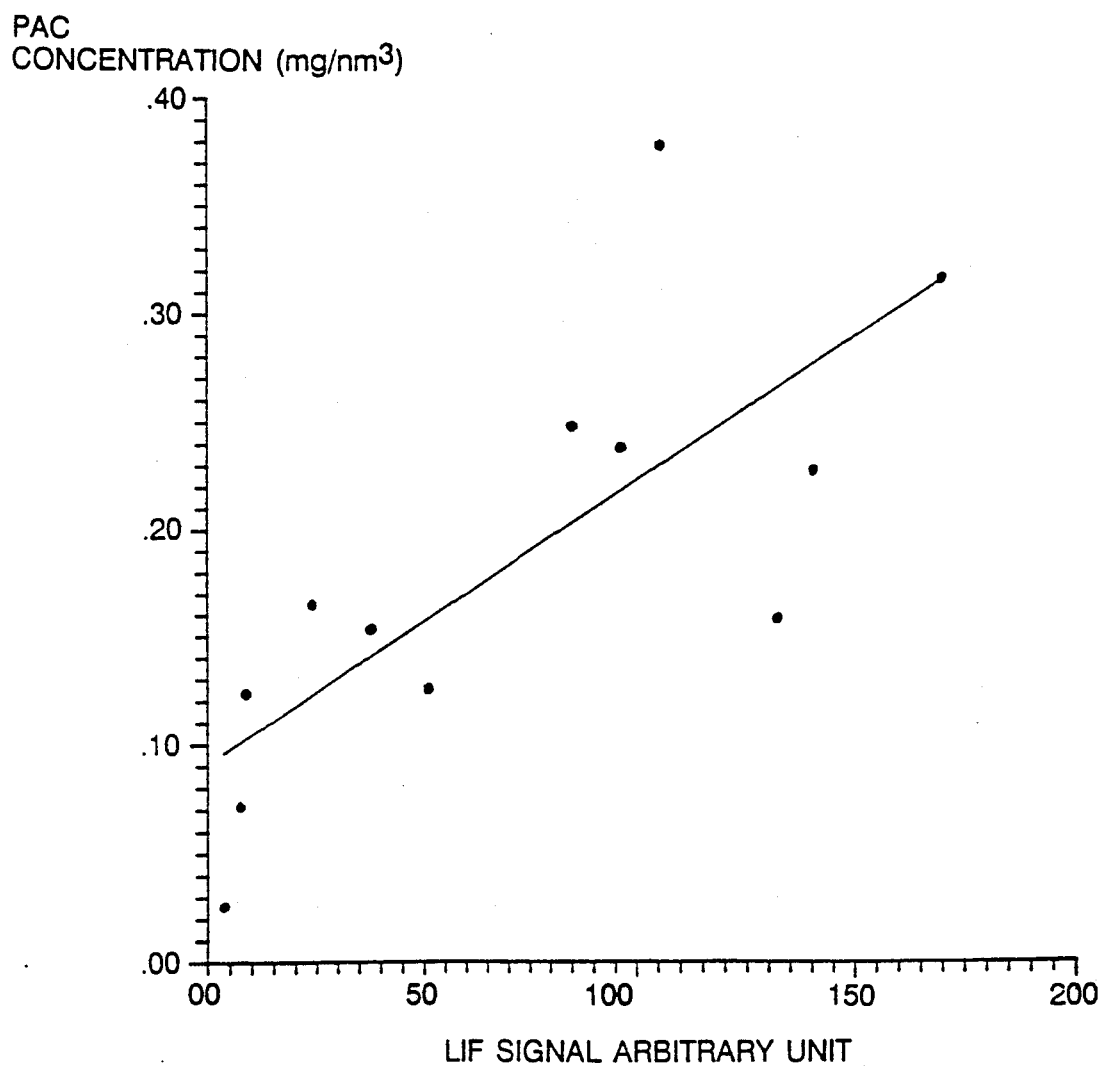

Referring now to FIG. 7-7a, graphs of the laser induced fluorescence intensity and the concentration of coronene (FIG. 7) and a sum of PAC's (FIG. 7a), are shown. PAC's included in the sum of PAC's are listed in Table 1, Example 4. Each data point in the graphs represents sampling at a different position along the effluent stream.

As the data shows, there is substantial correspondence in LIF signal intensity to the concentration of coronene (FIG. 7) and the sum of PAC's of Table 1 (FIG. 7a).

Example 4

Referring further to Table 1, data is given for the relative concentration (in mg/normal m$^3$) of various PAC's from the effluent of turbulent diffusion flames of various fuels, obtained by collection and chemical analysis as discussed above. All samples were collected from the same position along the effluent stream, at which the effluent temperature was 1200° C. In Run A, pure methane was employed as the fuel. In Run B, about 800 ppm toluene was injected into the methane. In Run C, less toluene, about 500 ppm, was injected. The toluene injected flames more closely approximate the combustion in commercial systems, e.g., of wastes, which often contain PAC's.

As the data indicates, the toluene doped flames (Runs B and C) produce larger amounts of PAC than pure methane flames (Run A). In all of the runs, significant amounts of high molecular weight PAC's were present.

Other embodiments are in the claims.

TABLE 1

|  | RUN A | RUN B | RUN C |
| --- | --- | --- | --- |
| Phenanthrene (3 rings) | 0 | 50.73371 | 0 |
| Anthracene (3 rings) | 0 | 37.45171 | 0 |
| Fluoranthene (4 rings) | 0.466369 | 95.72006 | 90.42092 |
| pyrene (4 rings) | 0.941431 | 47.1108 | 33.83611 |
| Chrysene (4 rings) | 0.016078 | 41.27587 | 30.4315 |
| Cyclopenta(cd)pyrene (5 rings) | 1.262762 | 36.10435 | 27.36008 |

TABLE 1-continued

|  | RUN A | RUN B | RUN C |
| --- | --- | --- | --- |
| Benzo(b)fluoranthene (5 rings) | 0.059428 | 20.34275 | 15.90194 |
| Benzo(k)fluoranthene (5 rings) | 0 | 10.73589 | 8.537797 |
| Benzo(a)pyrene (5 rings) | 0.201211 | 15.33316 | 11.94513 |
| Benzo(ghi)perylene (6 rings) | 0.591417 | 4.832319 | 3.853191 |
| 1,2,3, 1',2',3' diindopyrene (6 rings) | 0.00015 | 0.013092 | 0.01154 |
| Anthanthrene (6 rings) | 0.325189 | 6.002026 | 5.348541 |
| Coronene (7 rings) | 0.308809 | 3.738882 | 3.25369 |
| Alkylated coronene (7 rings) | 0.027424 | 2.559951 | 0 |
| Unknown compound | 0.126353 | 3.469245 | 1.943956 |
| benzo (a) coronene (8 rings) | 0.163502 | 1.895973 | 0 |
| Benzo (n) perylene (7 rings) | 0 | 3.480517 | 0 |
| Naphto coronene (9 rings) | 0.208072 | 0 | 0 |
| Ovalene (10 rings) | 0.067205 | 0 | 0 |
| Sumpac | 4.7654 | 380.8003 | 232.8444 |

What is claimed is:

1. A method for detecting the presence of polycyclic aromatic compounds in the effluent of a turbulent commercial combustion system for monitoring or controlling the composition of said effluent, comprising:
   directly, selectively detecting the presence in said effluent of high molecular weight polycyclic aromatic compounds having five or more rings by,
   selecting excitation radiation having a fluorescence excitation wavelength that induces substantial fluorescence by said high molecular weight polycyclic aromatic compounds having 5 or more rings in the gas phase, and
   selecting a position along the effluent system at which said high molecular weight polycyclic aromatic compounds having 5 or more rings may be present in sufficient amounts such that fluorescence from said effluent at said position at said excitation wavelength is predominantly from said high molecular weight polycyclic aromatic compounds having 5 or more rings when said high molecular weight polycyclic aromatic compounds are present in said amounts,
   illuminating said effluent at said position with said excitation radiation,
   detecting fluorescence from said illuminated effluent; and
   analyzing said fluorescence to directly, selectively determine the presence of said high molecular weight polycyclic aromatic compounds in said effluent.

2. The method of claim 1 further comprising detecting said high molecular weight polycyclic aromatic compounds having 5 or more rings in a concentration range of about 10 ppm or less.

3. The method of claim 1 comprising selecting said position along said effluent stream downstream of the flame or combustion region where said effluent has a temperature of less than about 1200° C. and higher than the temperature at which excessive sooting occurs.

4. The method of claim 1 wherein said effluent temperature is about 250° C.

5. The method of claim 1 wherein said effluent temperature is between about 250° C. to 1200° C.

6. The method of claim 1 wherein said analyzing further comprises analyzing the intensity of said fluorescence and correlating the intensity with the concentration of said high molecular weight polycyclic aromatic compounds having 5 or more rings.

7. The method of claim 6 comprising analyzing the intensity of said fluorescence to determine the concentration of particular high molecular weight polycyclic aromatic compounds having 5 or more rings.

8. The method of claim 6 comprising analyzing the intensity of said fluorescence to determine the concentration of the sum of high molecular weight polycyclic aromatic compounds having 5 or more rings.

9. The method of claim 1 further comprising correlating fluorescence from said high molecular weight polycyclic aromatic compounds having 5 or more rings with the presence of other polycyclic aromatic compounds.

10. The method of claim 0 further comprising correlating the intensity of said fluorescence with the concentration of said other polycyclic aromatic compounds.

11. The method of claim 9 or 10 wherein said other polycyclic aromatic compounds are selected from the group consisting of chlorinated dioxins and furans and PCB's.

12. The method of claim 1 further comprising:
   effecting the composition of said effluent in response to said detecting and analyzing.

13. The method of claim 12 wherein said effecting comprises injection of reactive species into said effluent.

14. The method of claim 13 further comprising selecting said position along said effluent stream such that injection of said reactive species can occur downstream of said selected position for real-time control of said effluent.

15. The method of claim 12 wherein said effecting comprises controlling the conditions of combustion.

16. The method of claim 1 wherein said high molecular weight polycyclic aromatic compounds have seven rings or more.

17. The method of claim 1 wherein said high molecular weight polycyclic aromatic compounds having 5 or more rings are selected from the group consisting of cyclopenta [cd] pyrene, 1,3 di-indopyrene, Benzo(b)fluoranthene, benzo(k)fluoranthene, Benzo(a)pyrene, Benzo(ghi)perylene, 1,2,3, 1',2',3' diindopyrene, Anthanthrene, Coronene, benzo(a)coronene, Benzo (n) perylene, Naphto coronene, and Ovalene.

18. The method of claim 1 wherein said illuminating comprises illuminating said effluent with radiation having a wavelength between about 400 to 515 nm.

19. The method of claim 18 wherein said wavelength is about 488 nm.

20. The method of claim 18 or 19 wherein said radiation is provided by a laser.

21. The method of any one of claim 1, 18 or 19 wherein said detected fluorescence is in the range from the illuminating wavelength to about 650 nm.

22. A method for detecting the presence of dioxin in the effluent of a turbulent commercial combustion system, comprising:
   directly, selectively detecting the presence of high molecular weight polycyclic aromatic compounds having five or more rings by
   selecting excitation radiation having a fluorescence excitation wavelength that induces substantial fluorescence by said high molecular weight polycyclic aromatic compounds having 5 or more rings in the gas phase, and selecting a position along the effluent stream downstream of the flame or combustion region where said effluent has a temperature of about 1200° C. or less and at which high molecular weight polycyclic aromatic compounds having 5 or more rings may be present in sufficient amounts such that fluorescence from said effluent, at said position, at said excitation wavelength is predominantly from said high molecular weight polycyclic aromatic compounds having 5 or more rings, when said high molecular weight polycyclic aromatic compounds are present in said amounts, illuminating said effluent at said position along the effluent stream with said radiation.

detecting fluorescence from said illuminated effluent, analyzing said fluorescence to directly, selectively determine the presence of said high molecular weight polycyclic aromatic compounds having 5 or more rings in said effluent, and indirectly detecting the presence of said dioxins by correlating the fluorescence from said high molecular weight polycyclic aromatic compounds having 5 or more rings with the presence of said dioxins.

23. A method for controlling the production of aromatic hydrocarbons in a turbulent commercial combustion system, comprising:

directly, selectively detecting the presence of high molecular weight polycyclic aromatic compounds having five or more rings by selecting excitation radiation having a fluorescence excitation wavelength that induces substantial fluorescence by said high molecular weight polycyclic aromatic compounds having 5 or more rings in the gas phase, and selecting a position along the effluent stream downstream of the flame or combustion region where said effluent has a temperature of about 1200° C. or less and at which high molecular weight polycyclic aromatic compounds having 5 or more rings may be present in sufficient amounts such that fluorescence from said effluent, at said position, with said excitation radiation is predominantly from said high molecular weight polycyclic aromatic compounds having 5 or more rings, when said high molecular weight polycyclic aromatic compounds are present in said amounts, illuminating the effluent at said position, detecting fluorescence from said effluent, analyzing said fluorescence to directly, selectively determine the presence of said high molecular weight polycyclic aromatic compounds having 5 or more rings in said effluent; and effecting the composition of said effluent in response to said detecting.

24. The method of claim 23 wherein said effecting comprises controlling the conditions of combustion.

25. The method of claim 23 wherein said effecting comprises injection of reactive species into said effluent.

26. The method of any one of claims 1, 2, 3, 22 or 23, wherein said selectively detected high molecular weight polycyclic aromatic compounds have seven rings or more.

27. The method of claim 26 wherein said excitation wavelength is in the range of about 400 to 515 nm.

28. The method of claim 27 wherein said excitation wavelength is about 488 nm.

29. The method of claim 28 wherein said selectively detected high molecular weight polycyclic aromatic compounds are in a concentration range of about 10 ppm or less.

30. The method of any one of claims 2, 3, 22 or 23 wherein said analyzing includes comparison of fluorescence detected from said effluent to the known fluorescence of high molecular weight polycyclic aromatic compounds having 5 or more rings in the gas phase.

31. The method of any one of claims 1, 2, 3, 22 or 23 wherein selecting a position along said effluent stream includes sampling and analyzing said effluent by means other than LIF.

* * * * *